United States Patent [19]

Giraud et al.

[11] Patent Number: 5,288,292
[45] Date of Patent: Feb. 22, 1994

[54] KERATOME WITH MINIATURE DIFFERENTIAL MICROMETER

[75] Inventors: Clarence E. Giraud, Mesa; Edward R. Perry; Russell G. Koepnick, both of Phoenix, all of Ariz.

[73] Assignee: Micro Precision Instrument Company, Phoenix, Ariz.

[21] Appl. No.: 985,338

[22] Filed: Dec. 4, 1992

[51] Int. Cl.⁵ .......................... A61B 17/32; G01B 3/18
[52] U.S. Cl. ...................................... 606/166; 33/814;
33/828; 33/512
[58] Field of Search ...................... 606/166, 167, 172;
128/774; 33/814, 821, 822, 828, 831, 512

[56] References Cited

U.S. PATENT DOCUMENTS

| | | | |
|---|---|---|---|
| 3,402,613 | 9/1968 | Neusel et al. | 33/814 |
| 4,173,980 | 11/1979 | Curtin | 606/166 |
| 4,423,728 | 1/1984 | Lieberman | 606/166 |
| 4,526,171 | 7/1985 | Schachar | 606/166 |
| 4,570,489 | 6/1988 | Berkman et al. | |
| 4,807,623 | 2/1989 | Lieberman | 606/166 |

FOREIGN PATENT DOCUMENTS

| | | | |
|---|---|---|---|
| 572506 | 3/1959 | Canada | 33/814 |
| 120472 | 12/1947 | Sweden | 33/822 |

Primary Examiner—Tamara L. Graysay
Attorney, Agent, or Firm—Cahill, Sutton & Thomas

[57] ABSTRACT

A keratome includes a miniature differential micrometer having a barrel, a middle sleeve, and a inner sleeve connected by a threaded shaft having threads of two different pitches. One end of each of the middle sleeve and inner sleeve is drilled and tapped undersize and is slotted to conform resiliently to the threaded shaft. The middle sleeve is attached to a keratome by set screws drawing the middle sleeve into tight contact with the body of the keratome. The adjustable plate in the keratome is attached to the inner sleeve.

20 Claims, 2 Drawing Sheets

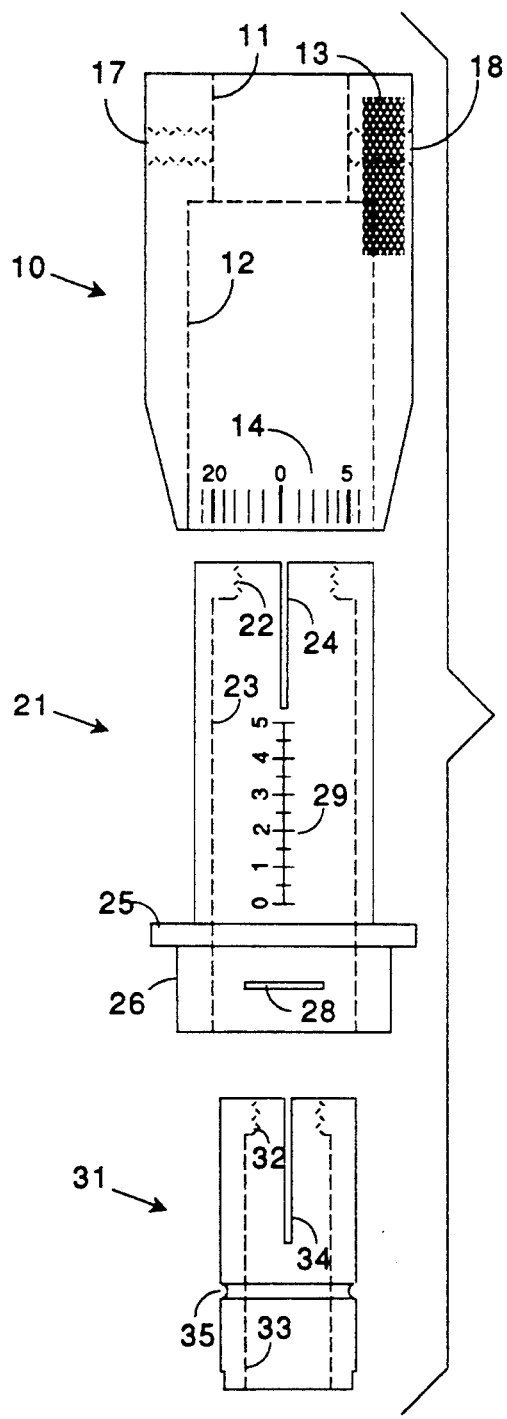
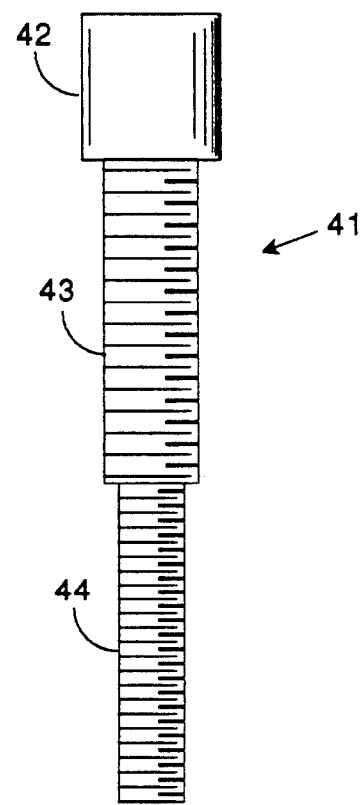
FIG. 1
FIG. 2

KERATOME WITH MINIATURE DIFFERENTIAL MICROMETER

BACKGROUND OF THE INVENTION

This invention relates to surgical apparatus and, in particular, to a miniature differential micrometer for a keratome.

A keratome is a surgical instrument for making thin slices of the cornea of the eye and resembles a tiny block plane having an overall length of about three centimeters. Unlike a block plane, the bottom of a keratome is not a single surface. An adjustable plate is located at the leading or front end of the keratome, followed by the cutting blade. Also unlike a block plane, the blade in a keratome oscillates from side to side at high speed to slice the corneal tissue.

In the normal cutting position of the keratome, the adjustable plate forms part of the bottom surface of the keratome and can be moved up and down, i.e. perpendicular to the bottom surface. (Any reference to direction is for the sake of description only. A keratome can be held and used for cutting in any orientation.) The adjustable plate is slightly trapezoidal in shape and one of the parallel edges of the plate is positioned adjacent the blade. The vertical spacing between the plate and the blade determines the depth or thickness of the cut.

The human eye is actually a compound Optical system including a fixed "lens," the cornea or outer surface, and a focusing lens. Severely myopic (nearsighted) patients often can have normal vision restored by thinning the cornea. In surgery on the cornea, the depth of cut is critical because the cornea of a human eye is typically 520 microns (0.020 inches) thick. In a procedure known as kerato-mileusis in-situ, the outer surface of the cornea, e.g. 150 microns, is removed in a first slice, a section 20–250 microns is removed in a second slice, and the first slice is re-attached to the eye. Obviously, the setting of the blade is extremely critical for each cut. The depth of cut must be known precisely and accurately.

In the past, keratomes have been provided with an adjustment screw having a fine thread, enabling small changes to be made in the depth of cut. The problem is knowing how deep the cut will actually be. Typically, a gauge is provided for measuring the displacement of the plate from the blade. The problem with a gauge is that it cannot withstand sterilization. Since the surgical field and all instruments must be sterile, adjusting the blade means placing the keratome in a non sterile gauge, setting the depth of cut by touching the plate with part of the gauge, and then sterilizing the keratome.

Thus, it is desired to have a keratome with an integral, calibrated adjustment. Micrometer adjustments of the prior art rely on a fine threaded screw but even this is not very accurate. For accurate correction of myopia, ophthalmic surgeons want an adjustment accurate to ±(2-5) microns. While micrometers capable of this accuracy are known, they dwarf the keratome in size and are unsuited to being incorporated into a keratome.

Berkman et al. U.S. Pat. No. 4,750,489—discloses a surgical knife for use in a procedure known as radial keratotomy in which shallow, radial slits are made in, but not through, the cornea. The knife includes a micrometer and electronics within the knife are used for "eliminating reliance on the accuracy of the adjusting screw." In other words, the micrometer is not sufficiently accurate for surgery on the eye. A calibration system is disclosed for sensing the zero or "datum" point on the extension of the blade from the end of knife. In surgery, the electronics in the knife indicate the amount the blade is extended.

The most accurate micrometers known are differential micrometers. These devices have a single screw with threads of two different pitches. The movement of the contact point in the micrometer is determined by the difference in pitch of the threads. For example, if one thread were twenty turns per inch (0.05 inches per turn) and the other thread were twenty five turns per inch (0.04 inches per turn), then one turn of the screw would produce a movement of 0.01 inches of the contact point. Differential micrometers of the prior art are typically four-six inches long, far too large for a keratome.

Differential micrometers cannot simply be scaled down in size. Everything that is made smaller is also made weaker. For example, tension nuts, needed to avoid backlash, break during use when a differential micrometer is made small enough to be incorporated into a keratome. (Backlash is movement of the contact without rotation of the barrel or no movement of the contact with some rotation of the barrel.)

Even if a small differential micrometer were available, the problems of calibration and sterilization remain. Surgeons want a device with a dial, easily read, that can be adjusted in the operating room, knowing that the cut will be the thickness indicated. In this way, two consecutive cuts of different thickness can be made without contaminating the keratome between cuts with a calibration gauge.

The dial should be easily read and provide the surgeon with a feel for how much the plate has been adjusted. Typically, the barrel of a micrometer moves as it is rotated to reveal more or less of a fixed scale. If the pitch of the thread on which the barrel turns is made arbitrarily fine, then the barrel moves little. Thus, there are contrary demands on the pitch of the threads: a larger pitch causes the barrel to move a greater distance while a smaller pitch increases the resolution of the micrometer.

In view of the foregoing it is therefore an object of the invention to provide a differential micrometer fitting on one end of a keratome.

Another object of the invention is to provide a keratome which is calibrated during manufacture and does not require re-calibration thereafter.

A further object of the invention is to provide a keratome which can cut with a resolution of one micron and an accuracy of ±(2-5) microns.

Another object of the invention is to provide a keratome which can be sterilized and used without further calibration.

A further object of the invention is to provide a miniature differential micrometer.

Another object of the invention is to provide a miniature differential micrometer having a relatively large longitudinal movement of the barrel in proportion to the movement of the contact point.

SUMMARY OF THE INVENTION

The foregoing objects are achieved in the present invention in which three concentric sleeves are attached to a shaft having threads of two different pitches. The outermost sleeve is fixed to one end of the shaft and turns the shaft within the other two sleeves. The middle sleeve has internal threads on one end thereof for engaging threads of a first pitch on the shaft. The innermost sleeve is attached to the adjustable plate at one end and has internal threads at the other end for engaging threads of a second pitch on the shaft. The second pitch is preferably finer than the first pitch, e.g. 65 threads per inch versus 61 threads per inch.

The threaded portion of each sleeve is drilled and tapped undersize and is slotted to provide slight resiliency, enabling the sleeves to engage their respective threads without backlash. The middle sleeve fits through a hole in the top of the keratome and has an annular shoulder on the outside thereof for engaging the body of the keratome. The middle sleeve is held in place by set screws through the body of the keratome engaging V shaped slots in the outer surface of the middle sleeve. The set screws are slightly out of alignment with the V, causing the shoulder to be drawn tightly down onto the body of the keratome. After the adjustable plate is set to zero displacement, it is attached to the third sleeve thereby calibrating the keratome. The spacing between a portion of the adjustable plate and the end of the middle sleeve is less than the maximum thickness of the cornea, preventing the plate from being raised above the blade a distance greater than the thickness of a human cornea.

BRIEF DESCRIPTION OF THE DRAWINGS

A more complete understanding of the invention can be obtained by considering the following detailed description in conjunction with the accompanying drawings, in which:

FIG. 1 is an exploded view of the three sleeves used in a differential micrometer constructed in accordance with the invention.

FIG. 2 is a threaded shaft for connecting the sleeves together.

DETAILED DESCRIPTION OF THE INVENTION

Figures 3, 4:
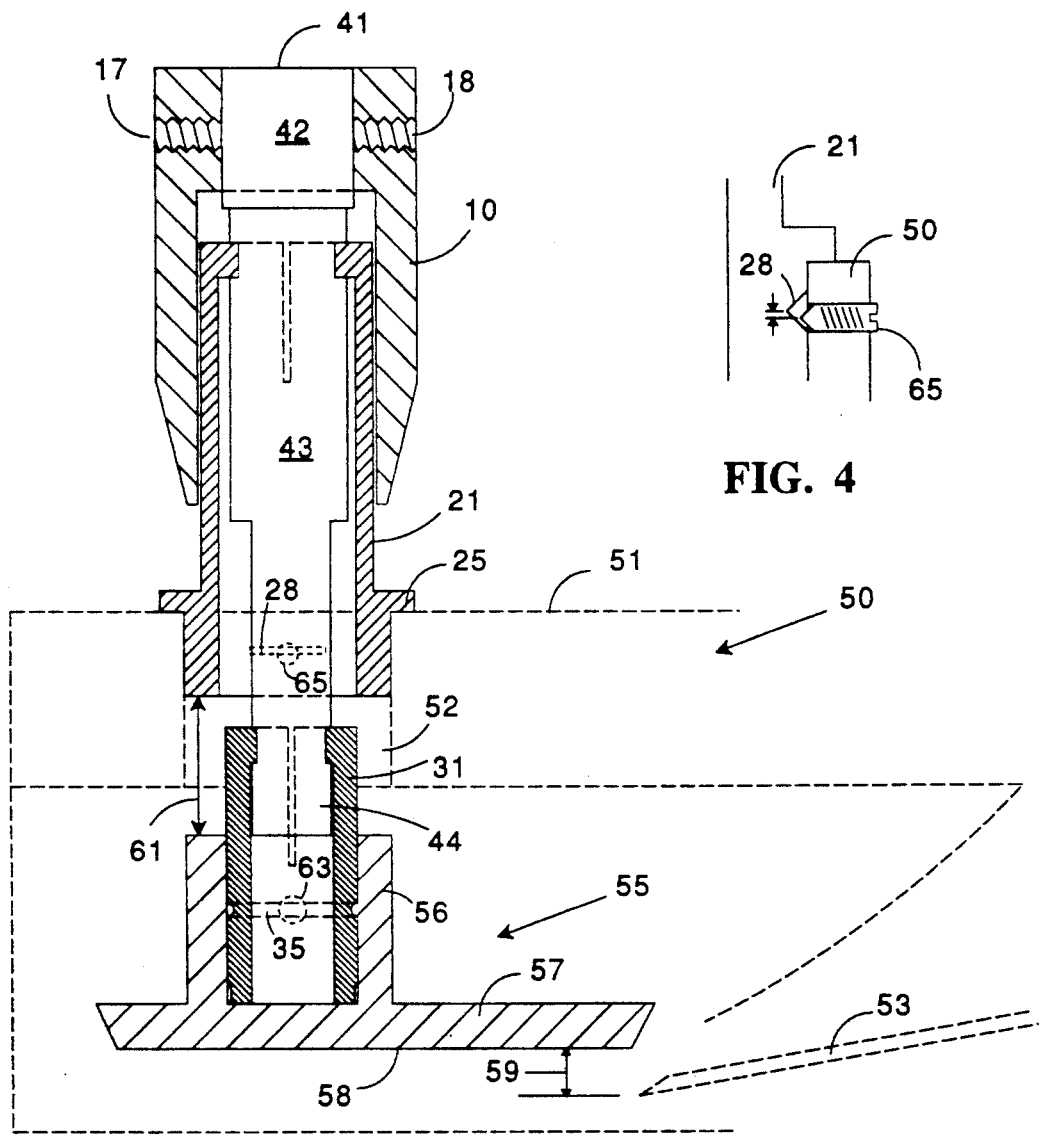
FIG. 3 illustrates a keratome including a miniature differential micrometer constructed in accordance with the invention.
FIG. 4 illustrates a detail of fastening the middle sleeve to the body of the keratome.

FIG. 1 is an exploded view of three concentric, partially overlapping sleeves used in a miniature differential micrometer constructed in accordance with the invention. The upper sleeve, referred to as barrel 10, includes a longitudinal bore of two different diameters in which bore 11 has a smaller diameter than chamber 12. The external surface of barrel 10 preferably includes knurling 13 to provide a secure grip for rotating barrel 10 by a surgeon. The lower end of barrel 10 is tapered and radial scale 14 is etched or printed at the end of barrel 10. scale 14 has twenty-five indicia uniformly spaced around the tapered end of barrel 10. Threaded bores 17 and 18 receive set screws (not shown) for holding threaded shaft 41 (FIG. 2).

The middle sleeve, referred to as micrometer insert 21, has an outside diameter slightly smaller than the inside diameter of chamber 12 of barrel 10. Threads 22 in the upper end of insert 21 have an inside diameter less than the inside diameter of chamber 23. Annular shoulder 25 on the outside of insert 21 has a larger diameter than end portion 26 which, in turn, has a larger outside diameter than the remainder of insert 21. This provides a thick walled end portion for connection to a keratome and a shoulder for precisely locating the middle sleeve.

A pair of shallow, V-shaped notches are cut into the outside surface of end portion 26. Notch 28, and another slot on the opposite side of insert 21, are used to secure insert 21 to the body of the keratome. Longitudinal scale 9 on the outside of insert 21 provides a coarse measurement of the displacement of the adjustable plate. As with differential micrometers and direct micrometers of the prior art, scales 14 and 29 cooperate to indicate the amount of displacement. Scale 29, labeled 0–5, representing 0–500 microns, provides a coarse measurement and scale 14, labeled 0–24 microns, provides a fine measurement.

The lower sleeve, referred to as adjustable plate insert 31, has an outside diameter slightly less than the inside diameter of insert 21. Threads 32 in the end of insert 31 have an inside diameter less than the inside diameter of chamber 33. Insert 31 fits within a cylindrical wall on the adjustable plate, as shown in FIG. 3. Annular groove 35 in the outside surface of insert 31 receives set screws (FIG. 3) for securing insert 31 to the adjustable plate.

Barrel 10 and inserts 21 and 31 are preferably made from titanium alloy. The threaded ends of inserts 21 and 31 are drilled and tapped undersize, which means that the tap hole for the threads is smaller than is normally used for a particular thread.

In standard hardware, the threads on a bolt have a V-shaped cross-section, as do the threads on a nut. The V's do not fully engage, i.e. the peak on a screw thread does not go all the way into the valley in a thread on a nut. The tap drill size typically gives what is known as a seventy-five percent thread, i.e. the peak on a screw thread only extends about seventy-five percent of the way into the valley in a thread on a nut. This reduces stress on the bolt and nut and makes the bolt much easier to rotate in the nut. It also permits backlash, which is irrelevant for fasteners but a serious problem in a micrometer.

If the sleeves were simply drilled and tapped undersize, i.e. for a one hundred percent thread, threads 22 and 32 would be an extremely tight fit for the threaded shaft. To alleviate the stress on the threaded ends of inserts 21 and 31, the threaded ends have longitudinal slots extending from the threaded end into the respective chambers of the inserts. The slots permit the ends of inserts 21 and 31 to expand or flex slightly to accommodate the threaded shaft. Tension nuts are eliminated and there is no backlash.

Insert 21 has slot 24 extending longitudinally a distance greater than the length of the threaded end portion. Similarly, slot 34 in insert 31 extends past threads 32 into the chamber portion of the insert. In a preferred embodiment of the invention, four slots are regularly spaced around each threaded end. The slots enable the respective ends to flex slightly and the threads engage the threaded shaft without binding and without backlash.

The following table is an example of suitable dimensions (in inches) for the sleeves.

TABLE I

|  | I.D. | O.D. |
| --- | --- | --- |
| bore 11 | 0.188 | 0.375 |
| chamber 12 | 0.257 | 0.375 |
| threads 22 | 0.145 | 0.250 |
| chamber 23 | 0.200 | 0.250 |
| shoulder 25 | 0.200 | 0.370 |
| end portion 26 | 0.200 | 0.300 |

TABLE I-continued

|  | I.D. | O.D. |
|---|---|---|
| threads 32 | 0.096 | 0.187 |
| chamber 33 | 0.120 | 0.187 |
| slots 24, 34 | 0.009 | — |

FIG. 2 illustrates a preferred embodiment of a threaded shaft for a miniature differential micrometer constructed in accordance with the invention. Shaft 41 includes a non-threaded end 42, a middle portion 43 threaded at a first pitch and a narrower end portion 44 threaded at a second pitch. Middle portion 43 has a pitch of 61 turns per inch and a screw size of 8-61. Narrower end portion 44 has a pitch of 65 turns per inch and a screw size of 4-65. Threaded shaft 41 is preferably made of a dissimilar metal alloy from inserts 21 and 31 to prevent galling action between the components. Preferably, threaded shaft 41 is made from Type 303 stainless steel.

Threaded shaft 41 connects barrel 10 to inserts 21 and 31 to form an extremely compact differential micrometer. Non-threaded or plain end 42 fits within bore 11 in barrel 10 with the remainder of shaft 41 extending through chamber 12 of barrel 10. Threads 22 of insert 21 engage middle portion 43 of threaded shaft 41. Similarly, threads 32 engage end portion 44 of threaded shaft 41. Thus connected, barrel 10 overlaps insert 21 and insert 21 overlaps insert 31.

The outside diameter of end 42 is very slightly (e.g. 0.0005 inches) less than the inside diameter of bore 11. End 42 is secured within bore 11 by set screws (not shown) in holes 17 and 18 in barrel 10. After inserts 21 and 31 are screwed into place, the differential micrometer is attached to a keratome as illustrated in FIG. 3. Keratome 50 includes front end 51 having hole 52 for receiving end portion 26 of insert 21. Plate assembly 55 includes cylindrical wall 56 and plate 57 formed as a single piece. The inside diameter of cylindrical wall 56 is slightly greater than the outside diameter of insert 31.

Major surface 58 of plate 57 is the reference plane from which the depth of cut is measured. Specifically, the depth of cut is the vertical displacement between major surface 58 the tip of cutting blade 53. This displacement, indicated by reference number 59, is preferably limited to approximately 450 microns. This provides a safety mechanism for using the keratome since it is unlikely that any cut would be made at a greater depth and the cornea is thicker than this maximum depth of cut. Plate assembly 55 is prevented from moving vertically a distance greater than about 450 microns by the height of cylindrical wall 56. That is, cylindrical wall 56 can move a distance, indicated by reference numeral 61, equal to or less than 450 microns.

The miniature differential micrometer is assembled as follows. Threaded shaft 41 is screwed into insert 21 as far as it will go and the lower end of insert 21 is placed in keratome 50. Plate assembly 55 is secured to insert 31 by set screw 63 through wall 56 engaging circumferential groove 35 around the outside of insert 31. Threaded shaft 41 is screwed all of the way into insert 31 by rotating both threaded shaft 41 and insert 21. Both are then unscrewed slightly to align notch 28 with set screw 65.

Insert 21 is secured to front end 51 of keratome 50 by set screw 65. As shown in greater detail in FIG. 4, notch 28 has a V-shaped cross-section, as does the end of set screw 65. However, notch 28 and set screw 65 are slightly out of alignment longitudinally, viz. set screw 65 is slightly below the center of notch 28. Thus, as set screw 65 is tightened, the bevels on notch 28 and set screw 65 force insert 21 down tightly against keratome 50. While a single set screw is believed sufficient, preferably a pair of set screws are used, holding insert 21 from each side of keratome 50.

At this point, displacement 59 is at or near maximum. One must now find zero displacement. This is done by measuring displacement 59 with a suitable gauge. If the reading is greater than the distance between the threads in lower portion 44 (about 390 microns), then set screw 65 is loosened and insert 21 and threaded shaft 41 are rotated together one full turn counterclockwise (as seen from above) to unscrew insert 31 from the end of the threaded shaft, thereby lowering plate assembly 55. Set screw 65 is then tightened again. Since one full turn is about 390 microns, plate 57 is now 390 microns closer to blade 53. To give a numerical example, suppose that the initial measurement indicated that displacement 59 was equal to 400 microns. After the described adjustment, displacement 59 equals 10 microns.

If displacement 59 is less than the distance between threads in lower portion 44, then insert 31 is rotated a fraction of a turn corresponding to the displacement. Insert 31 is removed by unscrewing threaded shaft 41 and the position of insert 31 is marked on wall 56, e.g. using one of the slits as a reference. Set screw 63 is loosened and insert 31 is rotated clockwise (or counterclockwise if the displacement is negative, i.e. if the plate is below the blade) a fraction of a turn. The fraction of the turn corresponds to the remaining displacement, about 9° for the remaining 10 microns $((10/390)*360° \approx 9°)$ in the numerical example. Set screw 63 is tightened and insert 31 is screwed onto threaded shaft 41.

The displacement is measured again and, if not now zero, the foregoing adjustment is repeated. If the displacement is now zero, then the maximum displacement can be set. As previously described, wall 56 engages the lower end of insert 21 to limit the depth of cut. As manufactured, wall 56 is not of a precise height, it is made slightly oversize. Without further adjustment, the maximum depth of cut would be an unknown amount less than the preferred 450 microns.

To adjust the maximum displacement to 450 microns, threaded shaft 41 is rotated counterclockwise to raise plate assembly 55, causing wall 56 to engage the lower end of insert 21. The displacement is measured on a gauge and the difference from 450 microns calculated. Plate assembly 55 is removed and the location of insert 31 marked or scribed on the part. Insert 31 is removed and plate assembly 55 is placed in a surface grinder to reduce the height of wall 56 by the measured difference. After being ground, insert 31 is replaced, set screw 63 is tightened, and plate assembly 55 is attached to threaded shaft 41. The keratome is placed in a gauge for a final check and, if all is well, the set screws are coated, e.g with lacquer or epoxy, and permanently tightened.

Barrel 10, which is not used during calibration, is placed on threaded shaft 41 and adjusted to the reading of the gauge. Set screws are placed in holes 17 and 18 and tightened. It is preferred that the barrel be set at its midpoint. While this does not change the percentage (relative) error in the readings, it significantly reduces the absolute error in displacement. For example, when the micrometer is calibrated at 225 microns, then the maximum absolute error over the entire range of settings is reduced from approximately ten microns to no more than five microns. The minimum error is zero microns at a setting of 225 microns.

In operation, as barrel 10 is rotated counter-clockwise (as seen from above), end portion 44 unscrews from insert 31 pushing insert 31 down. Threaded shaft 41 is also unscrewed from insert 21, moving shaft 41 up, lifting insert 31. Since the threads on middle portion 43 have a greater pitch than the threads on end portion 44, the upward motion of the shaft is slightly greater than the downward motion of insert 31. Because insert 21 is attached to keratome 50, the difference in motion between insert 31 and threaded shaft 41 results in a very slight net upward movement of plate assembly 55 as barrel 10 is rotated counter-clockwise.

As can be seen in the following tables, the difference in motion is such that one complete revolution of barrel 10 provides a net 25 microns of vertical displacement between blade 53 and plate 57.

TABLE II

| English Units | | |
|---|---|---|
| 61 turns/inch | = | 0.016393 inches/turn |
| 65 turns/inch | = | 0.015385 inches/turn |
| difference | = | 0.001009 inches |
| | = | 0.002562 cm. |
| | = | 25.62 microns per turn |

There are not exactly twenty five microns per revolution of the barrel, but the error is acceptably small. By design, the maximum displacement of the adjustable plate is limited to 450 microns, corresponding to eighteen revolutions of the barrel. If the micrometer is calibrated at zero displacement, then the maximum error, in absolute terms, is 0.62 times eighteen, or +11.23 microns at a reading of 450 microns; i.e. the dial reads 450 and the actual thickness is 461.23 microns. Stated in relative terms, the error is 2.5%. At 61 turns per inch, the barrel moves 0.295 inches in eighteen revolutions, while the plate moves 0.018 inches; i.e. the barrel moves 16.25 times the distance that the plate moves.

TABLE III

| Metric Units | | |
|---|---|---|
| 27 turns/cm. | = | 0.037037 cm./turn |
| 29 turns/cm. | = | 0.034483 cm./turn |
| difference | = | 0.002554 cm. |
| | = | 25.54 microns per turn |

The maximum error, in absolute terms, for a keratome using these metric threads is 0.54 times eighteen, or +9.77 microns at a reading of 450 microns; i.e. the dial reads 450 and the actual thickness is 459.77 microns. Stated in relative terms, the error is 2.2%. At 27 turns per cm., the barrel moves 6.67 cm. in eighteen revolutions, while the plate moves 0.046 cm.; i.e. the barrel moves 14.5 times the distance that the plate moves.

Barrel 10 rotates approximately eighteen times, for a displacement of 450 microns of plate 57, and moves slightly more than one quarter of an inch. In other words, the motion of barrel 10 is approximately fifteen times greater than the motion of plate 57. While relatively small in absolute terms, it must be borne in mind that the entire keratome is only approximately one and one-half inches long. As shown by Tables II and III, the error in displacement is slightly greater than two percent. This is significantly better than the ten to twenty percent error in keratomes of the prior art.

The invention thus provides provide a miniature differential micrometer which can be incorporated into one end of a keratome. The keratome is calibrated during manufacture, does not require re-calibration thereafter, and provides a resolution of one micron and an accuracy of ±(2-5) microns. The barrel of the micrometer has a relatively large movement in proportion to the movement of the contact point, providing feedback for the amount of adjustment of the plate in the keratome.

Having thus described the invention it will be apparent to those of skill in the art that various modifications can be made within the scope of the invention. For example, barrel 10 can be attached to threaded shaft 41 by press fit or by adhesive, instead of the set screws described. The micrometer can be "zeroed" at any point in its range. The miniature differential micrometer can be used anywhere extremely precise movement is needed, as in knives for radial keratotomy and in non-surgical applications such as optical instruments. The particular metals described are preferred for use in a keratome and are not critical. Also, the keratome can be made larger for sectioning other tissue.

We claim:

1. A keratome including a body containing a cutting blade, a plate having a major surface defining a reference plane, said blade positioned in said body adjacent one edge of said plate, and a differential micrometer attached to said body and to said plate for precisely moving said plate in a direction perpendicular to said plane, wherein said differential micrometer comprises:

a threaded shaft having a first portion without threads, a second portion having threads of a first pitch, and a third portion having threads of a second pitch;

a first sleeve having internal threads at one end and attached to said plate at another end;

a second sleeve having internal threads at a first end;

said second sleeve having a second end attached to said body and engaging the second portion of said threaded shaft with the internal threads on said first end; and said first sleeve fitting within said second sleeve and engaging the third portion of said threaded shaft with the internal threads on the end of said first sleeve.

2. The keratome as set forth in claim 1 wherein said differential micrometer further comprises:

a third sleeve having a bore in one end, said bore having an internal diameter fitting the outside diameter of said first portion of said threaded shaft, wherein said threaded shaft extends through said third sleeve.

3. The keratome as set forth in claim 2 wherein said first pitch is larger than said second pitch.

4. The keratome as set forth in claim 3 wherein said first pitch is 61 turns per inch and said second pitch is 65 turns per inch.

5. The keratome as set forth in claim 2 wherein said first pitch is 27 turns per cm. and said second pitch is 29 turns per cm.

6. The keratome as set forth in claim 2 wherein said first sleeve and said second sleeve each have at least one longitudinal slot extending through said threads on the respective ends of said first and second sleeves.

7. The keratome as set forth in claim 2 wherein the threads of said first sleeve and said second sleeve are drilled and tapped undersized.

8. The keratome as set forth in claim 2 wherein said first sleeve and said second sleeve are made from the same metal alloy and said threaded shaft is made from a dissimilar metal alloy.

9. The keratome as set forth in claim 8 wherein said first sleeve and said second sleeve are made from titanium alloy and said threaded shaft is made from stainless steel.

10. The keratome as set forth in claim 2 wherein said second sleeve has an annular shoulder adjacent said second end.

11. The keratome as set forth in claim 10 wherein said second sleeve includes V-shaped notches, one each on opposite sides of said second sleeve, said notches being located between said annular shoulder and said second end.

12. The keratome as set forth in claim 11 and further comprising two set screws in said body engaging respective notches in said second sleeve.

13. The keratome as set forth in claim 12 wherein said notches and said set screws are misaligned for drawing said shoulder tightly against said body as said set screws are tightened.

14. The keratome as set forth in claim 2 wherein said first sleeve has an annular groove in the outer surface thereof.

15. The keratome as set forth in claim 14 wherein said plate includes a cylindrical wall perpendicular to said plane and at least one set screw in said wall and engaging said annular groove for attaching said plate to said first sleeve.

16. A differential micrometer comprises:
   a threaded shaft having a first portion without threads, a second portion having threads of a first pitch, and a third portion having threads of a second pitch;
   a first sleeve having internal threads at one end and attached to said plate at another end;
   a second sleeve having internal threads at a first end;
   a third sleeve having a bore in one end, said bore having an internal diameter fitting the outside diameter of said first portion of said threaded shaft;
   said threaded shaft extending through said third sleeve;
   said second sleeve having a second end attached to said body and engaging the second portion of said threaded shaft with the internal threads on said first end; and
   said first sleeve fitting within said second sleeve and engaging the third portion of said threaded shaft with the internal threads on the end of said first sleeve.

17. The differential micrometer as set forth in claim 16 wherein the threads of said first sleeve and said second sleeve are drilled and tapped undersized.

18. The differential micrometer as set forth in claim 17 wherein said first sleeve and said second sleeve each have at least one longitudinal slot extending through said threads on the respective ends of said first and second sleeves.

19. The differential micrometer as set forth in claim 16 wherein said first sleeve and said second sleeve are made from the same metal alloy and said threaded shaft is made from a dissimilar metal alloy.

20. The differential micrometer as set forth in claim 19 wherein said first sleeve and said second sleeve are made from titanium alloy and said threaded shaft is made from stainless steel.

* * * * *